United States Patent [19]

Gregor

[11] 4,033,817
[45] July 5, 1977

[54] PRESSURE-DRIVEN ENZYME-COUPLED MEMBRANES

[76] Inventor: Harry P. Gregor, 150 Lakeview Ave., Leonia, N.J. 07605

[22] Filed: Nov. 7, 1975

[21] Appl. No.: 629,941

[52] U.S. Cl. .................................. 195/2; 195/29; 195/31 R; 195/31 F; 195/36 P; 195/63; 195/68; 195/DIG. 11

[51] Int. Cl.² .................. C07G 7/02; C12B 1/00

[58] Field of Search .............. 195/31, 31 F, 63, 68, 195/DIG. 11, 116, 2, 36 P, 29; 210/490; 264/331

[56] References Cited

UNITED STATES PATENTS

| | | | |
|---|---|---|---|
| 3,645,852 | 2/1972 | Axen et al. | 195/63 X |
| 3,705,084 | 12/1972 | Reynolds | 195/63 |
| 3,808,305 | 4/1974 | Gregor | 210/490 X |

OTHER PUBLICATIONS

Thang et al., Observations on the Activity of Enzymes after Filtration (and through) a Nitrocellulose Membrane, Biochem. Biophys. Res. Comm., vol. 31, No. 1, 1968, pp. 1–8.

Inman et al., The Immobilization of Enzymes on Nylon Structures and their Use in Automated Analysis, Biochem. J., vol. 129, 1972, pp. 255–262.

Olson et al., Immobilized Enzymes in Food and Microbial Processes, Plenum Press, N.Y. 1974, pp. 164, 165, 176, 177 & 180–184.

*Primary Examiner*—David M. Naff
*Attorney, Agent, or Firm*—Burgess, Dinklage & Sprung

[57] ABSTRACT

Pressure-driven enzyme-coupled membranes are prepared starting with a membrane filter having pores of appropriate, molecular dimensions and composed of a polymeric matrix, the activation of that matrix (where necessary) under pressure-driven conditions to impart to it appropriate groups capable of coupling to enzymes and similar substances of biological activity under pressure-driven conditions, and then employing this system under pressure-driven conditions to effect conversion processes which include the use of the coupled enzymes as the catalysts.

8 Claims, No Drawings

PRESSURE-DRIVEN ENZYME-COUPLED MEMBRANES

BACKGROUND OF THE INVENTION

The present invention encompasses a considerably broader range of matrix membranes, coupling reactions and enzymes than that included in my accompanying application, Ser. No. 629,940, filed Nov. 7, 1975, now pending, entitled ENZYME-COUPLED ULTRAFILTRATION MEMBRANES. It is directed to the preparation of a broad class of membrane filters to which enzymes and other molecules of similar catalytic activity are attached by chemical bonds, where the process of activation of the pore surfaces of these membranes for purposes of subsequent coupling (where such is needed) is carried out under pressure-driven conditions, and where the coupled enzyme system is used under similar pressure-driven conditions, namely by forcing the substrate to be treated through the membrane pores under pressure.

The conventional uses of immobilized enzymes are well known in the scientific, industrial and patent literature. The advantages of this general technique are, accordingly, well known. The usual technologies employed heretofore have been to use small particles of either natural or synthetic polymers or inorganic, porous materials. The enzymes are coupled thereto by chemical bonds or by the process of forming an insoluble gel in the presence of these enzymes, or by encapsulating the enzymes within small beads or within hollow fibers of porous nature, and the like. All of these conventional processes have their advantages and also their disadvantages. The purpose of the pressure-driven enzyme-coupled membranes of the present invention is directed to a novel method of preparing such membranes and to the membranes produced thereby, and to their use for a variety of applications. Their principal use is as a catalyst for carrying out chemical reactions. In the form which is described herein, the systems display a high capacity in terms of amount of enzyme contained therein and a high enzymatic activity, thus making these systems particularly useful for large-scale industrial processes. The enzymes so stabilized have, in addition to the before mentioned advantages, the usual, intrinsic advantages of stabilized enzymes in terms of their chemical and thermal stability.

SUMMARY OF THE INVENTION

In accordance with the present invention, I have found that enzyme reactors of high capacity and long term stability, of a kind which is particularly suitable for large-scale industrial use, can be prepared as follows. First, reasonably homoporous matrix membranes are prepared. These matrix membranes can be prepared from either homopolymers, from copolymers or from interpolymer mixtures. When prepared from homopolymers they must have an appropriate chemical and mechanical stability so that they can be used for periods of months in the presence of a solvent (usually water) without suffering significant changes in their porosity (volume fraction which is pores), pore diameter or dimensions. Accordingly, homopolymers which are employed must be insoluble. They can swell to but a limited extent in the solvent such as water. There are a limited number of homopolymers which are useful for the purposes of this invention. Cellulose is one homopolymer, and polyvinylbenzylchloride is another. The usual means of preparing membranes of these kinds is to cast them as a film from an appropriate solvent, then after part of the solvent has evaporated to form a gel-like film, the system is coagulated so as to produce a film having at least 50% of the volume of the film as pores of appropriate molecular dimensions. While there are many techniques which can be employed for the preparation of membranes of these kinds, a preferred procedure is to allow enough of the solvent to evaporate so that one forms a gel-like structure and then to introduce via the vapor phase a second solvent which acts to precipitate or coagulate the polymer. Introduction of the second solvent by the vapor phase helps to control the rate and extent of coagulation such as to produce highly homoporous membranes of desirable properties. Examples of films which can be made in this manner include those from cellulose dissolved in a mixture of dimethylsulfoxide and paraformaldehyde, prepared in accordance with the formulations of D.C. Johnson et al, (Institute of Paper Chemistry Technical Paper Series No. 5, April, 1975, Appleton, Wis.). Matrix polymer precipitation in this case is achieved by the use of either water or methanol vapor, and a film of desirable characteristics is produced along with the regeneration of the cellulose. Alternately, one can use a homopolymer or copolymer of vinylbenzylchloride, in this case polyvinylbenzylchloride or a copolymer of vinylbenzylchloride with styrene. These polymers are dissolved in a suitable solvent such as methylene chloride, the film is cast therefrom and then coagulation in the vapor phase employing methanol produces a membrane of the desired characteristics.

An alternate and a usually preferred method of preparing matrix membranes is to employ the general procedures prescribed by H. P. Gregor in U.S. Pat. No. 3,808,305 wherein membranes are cast from interpolymer mixtures. In a typical example, two parts of polyacrylic acid are dissolved in a suitable solvent such as dimethylformamide with one part of a film forming matrix polymer such as polyvinylidinefluoride (Kynar, Pennwalt Co.) together with a suitable epoxide cross-linking agent as described in U.S. Pat. No. 3,808,305 and this is then cast in the usual manner. In order to make these membranes of suitable porosity, while the cast membrane is partially dry, it is then coagulated by the introduction of a vapor which causes a partial coagulation but one which does not cause a loss of the structural integrity of the membrane. A suitable solvent in this case is water or another substance which causes the ionogenic polymer to become ionic, such as ammonia or triethylamine, following which final drying and curing by cross-linking of the film renders a membrane which has pores of appropriate dimensions while still containing a high concentration of carboxyl groups to which coupling reactions can take place. Similarly, amines such as polyvinylimidazole or poly-N-methylethylenimine can be employed in this formulation. Polymer mixtures which include polystyrenesulfonic acid provide for a highly polar negative charge within the membrane, and can be used together with a group capable of coupling such as polyacrylic acid. Accordingly, it is evident that by the judicious selection of matrix polymers and polymers to which coupling can take place, one can prepare a wide range of suitable matrix membranes. Thus, it is evident that a range of matrix polymers which have a wide range of hydrophilicity or hydrophobicity can be prepared, ranging from those which incorporated polystyrenesulfonic acid as a strongly hydrophilic polymer to those which contain polyvinylbenzylchloride as a highly hydrophobic polymer.

Similarly, a wide range of coupling chemistries are available. In some cases activation is required as in the treatment of cellulose by cyanogen bromide or the treatment of a polyvinylalcohol-containing membrane with cyanuric chloride. All of these procedures are well known to those versed in the art and are described in the literature, particularly in the book of O. R. Zaborsky ("Immobilized Enzymes", C.R.C. Press, Cleveland, Ohio, 1974). It is not the purpose of this invention to teach new chemical reactions for these activation reactions or the coupling reactions which follow, but rather to stress the unique combination of materials and procedures as taught herein, namely that the coupling and activation procedures can be carried out on a suitable membrane matrix under pressure-driven conditions.

The size of the enzyme molecules being coupled and the size of the membrane pores are important considerations in this invention. The size of enzyme molecules can be determined by many techniques, of which calculations based upon their rates of diffusion are but one. The size of membrane pores are usually determined by measuring the relative rates of diffusion or filtration of molecules of different size through the membrane pores and then employing hydrodynamic equations to calculate effective pore diameters. The procedures which are described by Kawabe et al. (J.Colloid Interface Sci. 21, 79 (1966)) are useful for this purpose. I have found that calculations which employ the parallel plate rather than the cylindrical pore models are more valid for the purposes of this invention. For example, I have found that when the diameter of the enzymes being coupled are one-third the diameter of the membrane pore, and when driving pressures not so high as to cause stress denaturation of the protein are employed, that one can effect a high degree of enzymatic coupling, such that an appreciable fraction (at least 30% of the total pore surface) is occupied by enzyme. I have found, accordingly, that a simple mechanical model suffices as a guide for these preparative procedures. If the pore walls are lined with enzymes by pumping in enzyme solutions from one side of the membrane to the other, the pore entrance will be blocked unless the pore diameter is at least three times that of the enzyme molecule itself. The application of this rule is not rigid because enzyme molecules are deformable and it is for this reason the pore should be at least twice the diameter of the enzyme molecule being attached to it, preferably some three to five times as large.

Another size consideration is that which arises due to the size of the substrate molecule. For example, if a large substrate molecule such as a protein is to be digested by a protease which is coupled to the membrane pores, then it is important that the large enzyme does not give rise to shear denaturation of the coupled enzymes while being forced through the pore.

In order to make appropriate use of the pressure-driven enzyme-coupled membrane concept, it is important that the matrix membrane have certain characteristics. First, its pores must be of molecular dimensions, at least twice the size of the enzymes to be accommodated therein and preferably 3 to 10 times the diameters of such enzyme molecules, but less than 20 times these diameters so that the membranes can have a high internal surface for coupling. Membranes having macroscopic pores of the dimensions of microns are not useful for the purposes of this application because their internal pore surface will be considerably smaller. Membranes with pores of about 15 to 200 Angstroms in diameter are preferred. The matrix membranes must be capable of withstanding the pressure gradient across them without collapse. Even at the relatively low pressure differences imposed in this system, namely from 10 to 150 psig, on the average, very soft gel-like structures collapse and thus the advantages of the method are lost. It is not necessary that the membrane withstand the pressure unsupported because the available membrane technologies allow one to support thin and fragile membranes on a variety of support materials. It is an important criterion, however, that the membrane pores remain substantially constant in size under conditions of use. An auxiliary requirement is that a substantial part of the interior pore surface be available for the coupling of enzyme molecules. Having a large number of very fine pores which are permeable to water but not to the enzyme molecule is not desirable.

The number of homopolymers which can be used for these purposes is limited. For example, the homopolymer polyvinylidenefluoride (Kynar, Pennwalt) and also the copolymer of acrylonitrile-vinylchloride (Dynel, Union Carbide) are both excellent film formers and have many of the requisite properties desired. However, they do not possess of themselves groups which afford the convenient coupling of enzymes, and are difficult to activate because of their high chemical resistances. On the other hand, cellulose nitrate is an excellent film former and has been used traditionally to form matrix membranes of the kind desirable for this process, but this polymer is not of sufficient chemical stability as such for use. The homopolymer cellulose does have the requisite chemical stability, it can be formed into membranes of appropriate properties either through its regeneration from cellulose acetate, or it can be formed directly by dissolution of cellulose in the dimethylsulfoxide-paraformaldehyde solvent system. Cellulose also is capable of being activated by a number of different agents for enzymatic coupling, and has been used widely for this purpose in its various forms. However, cellulose has a limited chemical stability. In addition, because of its nature, it appears to be capable of a limited reaction or coupling with carbohydrases and similar enzymes and thus may not be the preferred matrix polymer for enzyme reactors involving these enzymes. Further, cellulose itself is subject to decomposition by cellulases and for this reason is undesirable in certain specialized applications.

The interpolymer system, on the other hand, affords one the chemical stability of an insoluble and chemically resistant film-forming polymer when combined with a second polymer capable of chemical coupling to enzymes: where needed, one can also employ cross-linking agents to produce a material of the requisite properties. This interpolymer technique has already been highly developed by Gregor (U.S. Pat. No. 3,808,305).

The reactive polymers which can be part of an interpolymer mixture include cellulose, polyvinylbenzylchloride and its copolymers, poly-p-aminostyrene and its copolymers, copolymers of methacrylic acid with the fluoranilide adduct of methacrylic acid, polythiolstyrene, polyacrylic acid and its copolymers, the homopolymers and copolymers of maleic anhydride, poly-N- vinylimidazole, poly-N-methylethyleneimine and linear polyethyleneimine. In addition, one can also use polymers in the interpolymer mixture, ones which act to control the environment within the membrane pore, the so-called micro-environment of the coupled enzyme. Here one can employ the strongly acidic polymer polystyrenesulfonic acid, the strongly basic polymer poly-N-methylimidazolium chloride, as examples. The use of weak base and weak acid polymers have been enumerated above. Finally, if one wishes to make the micro-environment more hydrophobic, addition of acyl substituted polystyrene or its copolymers affords an excellent means to accomplish this, where the length of the hydrocarbon chain can be controlled at will.

The coupling of insoluble polymers to enzymes can occur through the amino group of the enzyme, through its carboxyl groups, through its tyrosine residues or through its mercapto groups. The most common means of coupling are achieved through the amino group of the enzyme, and for this the cyanogen bromide, anhydride, cyanuric chloride, and glutaraldehyde coupling procedures are well known. The diazonium coupling procedure is employed for coupling through the tyrosine residues and the isocyanide or Ugi reaction couples through the carboxyl groups. Thiol groups couple through the mercapto residues of the enzyme. On the other hand, by the use of Woodward's reagent K one can couple either with the amino group or the carboxyl group of the enzyme. Also, carboxylic groups on the matrix can be treated with carbodiimide to couple an enzyme either through the amino or carboxylic group.

One of the principal areas of application of these pressure-driven enzyme-coupled membrane systems are those to the cane and beet sugar industries, the corn processing industries, and their employment in the pressure-driven enzyme-coupled form is particularly advantageous. Certain enzymes of this class are usually adaptable to coupling by the use of a copolymer of methacrylic acid-3-fluoranilide which is subsequently nitrated, as described by G. Manecke (Pure and Applied Chemistry, 4, 507, (1962)). This polymer can be dissolved along with polyvinylidenefluoride (Kynar, Pennwalt) in a solvent mixture, a film is then cast, partially dried and then coagulated to form the desirable homoporous film. This membrane is already activated so that the direct coupling of enzymes to it follows, in this case through the amino group of the enzyme. Or, a copolymer of methacrylic acid and methacrylic acid-3-fluoranilide is prepared, combined with the same matrix polymer to form a film of appropriate porosity and then subsequently nitrated, activating the fluoranilide groups followed by coupling. The enzymes which are particularly amenable to this coupling procedure include dextranase, invertase, cellulase, dextran sucrase, alpha galactosidase, alpha amylase and glucose oxidase.

Procedures particularly amenable to employment in pressure-driven enzyme-coupled systems where coupling is through the diazonium linkage can employ interpolymer mixtures of Kynar and polyaminostyrene. Interpolymer films which contain cellulose can use cyanogen bromide to react with the cellulosic portion of the matrix film, and then treatment with p-phenylenediamine or benzidine, followed by treatment to form the diazonium salt allows for direct coupling. The enzymes which are particularly amenable to diazonium coupling include invertase, alpha amylase, beta amylase, glucose isomerase, amyloglucosidase and beta galactosidase. The reaction of cellulose with titanium tetrachloride can be employed to couple invertase, alpha amylase, amyloglucosidase and glucose oxidase. Finally, interpolymer membranes containing polyamines can be treated with glutaraldehyde to couple beta galactosidase and glucose oxidase. Accordingly, coupling of these carbohydrases and related enzymes follows directly and is particularly convenient when employing the pressure-driven enzyme-coupled membrane systems.

Another particularly useful embodiment of this invention is that wherein several enzymes are coupled to the same membrane or a series of membranes, used one after the other to effect a specific conversion. In this case 4 enzyme-coupled membranes were prepared, one with trypsin, a second with chymotripsyn, a third with aminopepsidase M and a fourth with prolidase. All of these membranes were prepared using cyanogen bromide activation followed by coupling. Upon the serial recirculation of solutions of polypeptides or proteins through this series of membranes, a complete amino acid hydrolysis resulted. Since the enzymes were entirely immobilized, since they could not attack one another and would not leach from the membranes, a complete digestion was effected without contamination. This form of enzymatic hydrolysis is particularly useful for analytical purposes because the amino acids that are usually completely or partially destroyed by conventional acid hydrolysis prior to their determination, namely tryptophan, tyrosine, serine, asparagine and glutamine are not destroyed in this procedure. In subsequent experiments, mixtures of these 4 enzymes were coupled simultaneously and, in yet others, dilute solutions of each of the enzymes were serially coupled to the same membrane. Since the procedures of this invention involve a rapid coupling to a rigid matrix which acts to isolate the enzymes and inhibit autodigestion and mutual digestion, a particularly useful and compact polypeptide and protein digestion system results.

Many applications of this multi-enzyme system are available. For example, it has been established that many substances which give rise to allergies and are thus antigenic do so because they are contaminated with small traces of foreign proteins. For example, penicillin and related antibiotics are often contaminated with a small amount of protein arising either from the initial enzymatic method of production or the conversion of penicillin to related compounds. Thus, the treatment of penicillin solutions to remove all traces of proteins can be effected by this multiple enzymatic reactor. Similarly, many other substances which contain small amounts of protein, ones which are difficult to remove by conventional means are amenable to treatment by this procedure. They can be used to decompose traces of protein present in commercial preparations of the alginates to produce compounds which do not possess a protein antigenicity.

The pressure-driven enzyme-coupled membranes of this invention are useful also for a number of important industrial processes in the drug and fermentation industries. One important area of application involves the use of such coupled enzymes to produce valuable derivatives from a variety of snythetic and natural products. A specific example is the use of membranes incorporating an acylase enzyme capable of the conversion of penicillin to 6-aminopenicillanic acid, also referred to as 6-AMP or 6-APA. This valuable derivative is produced from penicillin obtained by fermentation by the use of conventional fermentation processes. Pressure-driven enzyme-coupled reactors are important here because of their high capacity, reactivity and stability and the high purity of the products prepared thereby.

The examples given below are taken from laboratory studies and are representative of what can be obtained also under pilot plant and full-scale plant conditions. Since the process, in essence, consists of pumping a solution containing a given substrate through the membrane to which the enzyme is attached, the same process takes place on a large scale as on a small one. Accordingly, the scaling up of these processes offers no problem, another one of its advantages. In conventional fermentation, as an example, the prediction of the parameters of a large-scale fermentation process from those obtained in small laboratory fermenters is hazardous.

Many mechanical configurations are available for use with the objects of this invention. The devices employed are those which are commonly employed in conventional ultrafiltration and reverse osmosis processes. These include the conventional plate and frame devices, the spiral wound devices, the hollow fiber devices, the tube devices and the tubelet devices, all of which are well-known in the technical and patent literature. Since the purpose in any commercial fermenter is to obtain the highest capacity in terms of catalytic activity at the lowest cost, and since the cost of the enzyme is dependent upon other considerations, it is obviously advantageous to minimize the cost of the remainder of the equipment. The enzyme-coupled pressure-driven ultrafiltration membranes which are the objects of these inventions are unique in that devices can be made wherein the cost of the membranes, the cost of coupling and the cost of the mechanical equipment will be, it is estimated, substantially less than the cost of the enzyme itself unless one is dealing with a particularly inexpensive enzyme. Since one can include in such systems large membrane area and volume in a relatively small and simple device, the pressure-driven system has many and obvious advantages over all other configurations.

One of the obvious disadvantages, if such it is, of the pressure-driven ultrafiltration process involving coupled enzymes is that solutions containing particulate matter, suspended solids and the like, whose diameters are larger than the diameter of the pore openings, cannot be processed. It is necessary, as a consequence, to have available a process which will render these crude process streams capable of treatment. For this purpose the fixed-charge ultrafiltration membranes of Gregor (U.S. Pat. No. 3,808,305) offer an ideal pretreatment and have been used for such purposes.

Another advantage of the teachings of this invention is that one can obtain a high catalytic capacity per unit volume of reactor. Membranes have been prepared where at least 20% and as high as 60% of the dry weight of the finished membrane is the weight of the enzyme itself. This high capacity rises from the very large inner pore surface of the membrane and the pressure-driven method of coupling. The conventional microporous filter media which have pores in the micron size do not possess this large capacity and consequently systems made with their employment are not comparable to those of this invention.

The following examples are provided to more fully illustrate the invention. It will be understood that, because the examples are illustrative, they are not to be construed as limiting the invention, except as defined by the appended claims. All compositions are parts by weight, except where otherwise expressly stated.

EXAMPLE 1

A membrane was prepared from a 1:1 mixture of Kynar and cellulose in MSO-paraformaldehyde solution, allowed to dry for 2 min. in air, covered and allowed to equilibrate in the solvent vapor for 1 hour and then coagulated with water vapor and washed to have a thickness of 20 microns, a water content of 90% and a hydraulic permeability of 4.5 liters per hour at 50 psig pressure for an 11.3 $cm^2$ area. Activation by cyanogen bromide (40 mg CNBr in pH 11 water) was performed at 50 psig for 25 minutes. The membrane was washed for one minute in a 0.1 M phosphate buffer at pH 7.5 and then a solution consisting of 50 mg of the enzyme horse liver alcohol dehydrogenase in 100 ml of the same buffer was passed through at 50 psig. The membrane was then stored in this effluent for 24 hours at 4° C, then washed with water and its protein content was found to be 18% of the dry weight of the membrane.

The activity of this enzyme was determined using the standard procedures described in the Worthington Biochemical Corporation Manual (Freehold, N.J., 1972). The free solution activity of this horse liver alcohol dehydrogenase was determined at pH 7.5 in the phosphate buffer employing NAD as a coenzyme and with ethanol as substrate. The free solution activity of this enzyme was 0.31 units/mg and at 100 psig substrate pressure the activity of the coupled enzyme was 0.19 units/mg.

EXAMPLE 2

Jack bean urease (Worthington Biochemical) was coupled to a Kynar-cellulose membrane as prepared in Example 1 using cyanogen bromide activation under 50 psig pressure. The membrane had a hydraulic permeability corresponding to an average pore diameter of 300 AU. This enzyme has a molecular weight of 483,000 and is sensitive to traces of metal being present, so all experiments were carried out in the presence of 0.001 M EDTA. After the membrane was washed with cold water for 1 minute after activation, a solution of 50 mg of urease in 100 ml of 0.02 M phosphate buffer at pH 7.0 was passed through at 25 psig. The membrane was then stored in the effluent from the coupling reaction at 4° C overnight, then washed thoroughly with buffer. Its protein content showed that 55% of the weight of the dry membrane was protein. Its activity was determined by titration for the ammonia formed as a result of the decomposition of urea following the procedure in the Worthington Biochemical Corporation Catalogue (Freehold, N.J., 1972). Using this test, it was found that the activity of urease in the coupled state was 60% that of the free enzyme.

EXAMPLE 3

Glucose oxidase from *A. niger* (Worthington) was coupled to the cellulose-Kynar membrane of Example 1. After activation with cyanogen bromide and washing with cold water for one minute, 40 mg of glucose oxidase in 100 ml distilled water was passed through at 70 psig. The membrane was then stored in this effluent for 24 hours at 4° C, then washed thoroughly. Its protein content as determined by Lowry was 4.4 mg or 42% by weight of the dry membrane. Its activity was determined by the Worthington procedure but in the absence of horseradish peroxidase because the hydrogen peroxide formed would not inhibit the enzyme but be removed under the pressure-driven conditions employed. Accordingly, using the standard 18% solution of glucose as substrate and employing pure oxygen as pressurization gas so the oxygen content would not be rate-limiting, the rate of production of peroxide was measured and found to be 80% of that of the native enzyme.

EXAMPLE 4

In another modification of the present invention, a penicillin acylase was coupled to a membrane containing maleic anhydride groups under pressure-driven conditions. A film was prepared from 2 parts of a copolymer of vinylmethylether and maleic anhydride in equal molar amounts and combined with one part of Kynar dissolved in a mixture of hexamethylenephosphoramide and DMF together with an epoxide cross-linking agent, and the membrane cast therefrom was dried partially. After 10 minutes of drying in dry air at 60° C, the membrane was sprayed with a fine mist of toluene which caused a partial coagulation of the film, following which drying to effect a final cure was completed to produce a highly porous film. The coupling of penicillin acylase was achieved by dissolving 1 gram of this enzyme having a specific activity of 15 units/mg in 100 ml of a pH 6 buffer, wetting the membrane with this buffer which caused it to swell and then recirculating the enzymatic solution through the membrane at 4° C for a period of 2 hours at 40 psig. The pH was kept constant by the addition of dilute base. After a few moments the membrane had swelled sufficiently so that the solution of enzyme could be pumped through the membrane readily. The membrane continued to swell and its hydraulic permability increased. The final membrane has a protein content of 30% and its enzymatic activity was 45% of the activity of the same amount of native enzyme. For the production of 6-AMP from penicillin G, 100 g of the substrate 1 liter of water at constant pH 7.8 was passed through the membrane at 70 psig and at 38° C for 2 hours. It was found that the yield of product was 88% of theoretical.

EXAMPLE 5

A penicillin acylase derived from *E.coli* was coupled to the cellulose-Kynar membrane of Example 1. This membrane was activated by treatment with cyanogen bromide (40 mg in 100 ml at pH 11 kept constant by the addition of base) at 70 psig, following which the membrane was washed for 1 minute, and was treated with a solution of the enzyme in a phosphate buffer at pH 5.5, and containing 5 grams of enzyme in 200 ml of this solution. After pumping this solution through the membrane at 70 psig, followed by incubation overnight at room temperature and washing, the film obtained had 31% of its dry weight as enzyme protein. In a typical application of this membrane, 1 gram of the sodium salt of 7-(2-thienyl)-acetamidocephalosphoranic acid was treated at pH 7.5 at 37° with this enzyme-coupled membrane at 50 psig to produce 7-ASP in a yield of 98% after 10 minutes of reaction. In this experiment the effective area of the membrane was 11 cm$^2$, the amount of enzyme bound was 3.5 mg and its activity was 60% that of the native enzyme in this reaction.

EXAMPLE 6

A carboxylic membrane was prepared by the dissolution of 2 parts of polymethylacrylic acid to one part of polyvinylidenefluoride (Kynar, Pennwalt) together with an epoxide (0.1 part) cross-linking agent in a 10% solution of hexamethylenephosphoramide and DMF. The membrane was cast, allowed to dry partially at 60° C, then coagulated with water vapor to increase its porosity and finally cured at 120° C after drying at 60° C was completed. When wetted with water, the membrane had a water content of 80% and a hydraulic permeability corresponding to a pore diameter of 180 A.U. To prepare the enzyme-coupled membrane, 5 volumes of a 25% aqueous glutaraldehyde solution and 5 volumes of diaminopentane were added to 50 ml of water, the total volume made up to 100 ml and the pH adjusted to 6. This solution was pumped through the membrane at room temperature at 70 psig for 2 hours, the membrane then washed with pure pH 6 buffer, and then a 0.5% solution of an acylase preparation obtained from *E. coli* dissolved in 1 liter of pH 5 buffer was passed through the membrane for 3 hours at room temperature and at 60 psig. After washing with water it was found that the protein content of the membrane corresponding to 20% by weight of the dry membrane. The activity of the membrane was such as to correspond to a conversion rate of 200 micromoles per minute per gram of dry membrane of a 5% solution of K benzylpenicillin at pH 7.8 at 37° C, carried out at 30 psig, and with greater than 95% conversion.

EXAMPLE 7

A membrane was prepared as in Example 1 but with a 2:1 ratio of Kynar to cellulose to obtain a film of 180 AU pore diameter. After activation with cyanogen bromide and one minute of washing with water, all at 70 psig, the membrane was treated with a solution of p-phenylenediamine (100 mg in 100 ml) at pH 8.0 for 10 minutes, also at 70 psig, then incubated overnight, all at room temperature and, in the case of the last treatment, in the dark. Then after washing with water and 1 M sodium chloride, and then water again, the membrane was diazotized by treatment with 2 N hydrochloric acid at 0° C for 30 minutes. Then 5 ml of 14% sodium nitrite was added to the acid solution slowly, the membrane kept in this solution for one hour and then washed with 0.3% sulfamic acid at 0° C. Then the membrane is treated with a solution of the enzyme glucose isomerase (40 mg in 100 ml of pH 8.5 buffer) at 0° C at 30 psig for 1 hour of recirculation, followed by overnight incubation at 4° C. After washing with distilled water at 50 psig, the enzyme-coupled membrane was then treated with 0.5 sodium chloride solution. In use, the membrane was subjected to a 0.5 M solution of glucose at pH 8.0 at 60° C and at 30 psig to produce a fructose-containing effluent. The original activity of this enzyme was 15 units/mg and of the coupled enzyme was 13 units/mg. The loading of enzyme was 18% by weight of the dry membrane.

In the process of the invention as illustrated hereinabove, any superatmospheric pressure can be employed to accelerate the passage of activating liquid and/or of enzyme through the membrane although a pressure of at least about 10 psig, especially about 30 to 120 psig, gives particularly good results. For the solution of material acted upon by the enzyme-coupled membrane, a pressure of at least about 5 psig is desirable. The pressure or potential, instead of being of a pneumatic or hydraulic type, can be of an electrical nature, i.e. as in the well-known phenomenon of electro-osmosis and/or electrophoresis wherein an electrical potential is imposed across a membrane or filter and combinations of the activation-coupling and use operations effected in that manner. Thus, for example, with chymotrypsin coupled following activation with cyanogen bromide a current which produces a flow of solution through the membrane comparable to that due to a pressure gradient of 70 psi produces a system whose enzymatic activity is nearly the same as one prepared under 70 psig.

It will be appreciated that the instant specification and examples are set forth by way of illustration and not limitation, and that various modifications and changes may be made without departing from the spirit and scope of the present invention.

What is claimed is:

1. A process for effecting an enzymatic reaction comprising forcing a solution of an activating agent through a homoporous ultrafiltration membrane under a pressure equivalent to at least about 30 psig, thereby to form activated sites, the membrane having pores of about 15 to 200 Angstroms in diameter, forcing a solution of an enzyme through said membrane under a pressure equivalent to at least about 10 psig, the activated sites being chemically reactive with said enzyme thereby chemically to couple said enzyme to said membrane, and forcing a substrate solution through said membrane under a pressure equivalent to at least about 5 psig, said substrate solution containing a material which is capable of being converted by said enzyme, whereby said enzyme-coupled membrane effects said enzymatic conversion of said material.

2. The process of claim 1, wherein said membrane has pores averaging in size from about 3 to 5 times the diameter of said enzyme.

3. The process of claim 2, wherein the activating agent is forced through said membrane under a pressure equivalent to about 70 to 120 psig, and the enzyme is forced through said membrane under a pressure equivalent to about 70 to 120 psig.

4. The process of claim 1, wherein said enzyme solution contains a plurality of proteases, said material being contaminated with at least one protein or polypeptide, whereby said contaminant is enzymatically converted.

5. The process of claim 1, wherein said enzyme is an amylase, and said material is soluble starch, whereby said starch is enzymatically converted into glucose.

6. The process of claim 1, wherein said enzyme is glucose isomerase, and said material is glucose, whereby said glucose is partially enzymatically converted into fructose.

7. The process of claim 6, wherein the solution of glucose is produced by passing soluble starch through a membrane coupled to an amylase.

8. The process of claim 1, wherein said enzyme is a penicillinacylase, and said material is penicillin, whereby the penicillin is converted into penicillanic acid.

* * * * *